United States Patent [19]

Obermeier et al.

[11] Patent Number: 4,681,931
[45] Date of Patent: Jul. 21, 1987

[54] PROCESS FOR THE ISOLATION AND PURIFICATION OF ALPHA-INTERFERONS

[75] Inventors: Rainer Obermeier, Hattersheim am Main; Ingeborg Salomon, Wöllstadt; Jürgen Ludwig, Brachttal, all of Fed. Rep. of Germany

[73] Assignee: Hoechst Aktiengesellschaft, Fed. Rep. of Germany

[21] Appl. No.: 741,865

[22] Filed: Jun. 6, 1985

[30] Foreign Application Priority Data

Jun. 8, 1984 [DE] Fed. Rep. of Germany ....... 3421302

[51] Int. Cl.$^4$ .................... C07K 15/26; A61K 45/02; C12P 21/00
[52] U.S. Cl. .................... 530/351; 424/85; 435/68
[58] Field of Search .................... 424/85; 435/68, 811; 530/351

[56] References Cited

U.S. PATENT DOCUMENTS 4,343,735  8/1982  Menge et al. .................... 530/351
4,450,103  5/1984  Konrad et al. .................... 435/68
4,462,940  7/1984  Hanisch et al. .................... 424/85

OTHER PUBLICATIONS

L. S. Lin, Characterization of the Heterogeneous Molecules of Human Interferons: Differences in the Cross-Species Antiviral Activities of Various Molecular Populations in Human Leukocyte Interferons, J. General Virology, vol. 39, pp. 125–130, 1978.

*Primary Examiner*—Blondel Hazel
*Attorney, Agent, or Firm*—Finnegan, Henderson, Farabow, Garrett & Dunner

[57] ABSTRACT

The invention relates to a process for the isolation and purification of α-interferons generated by plasmids from bacterial cultures which have been modified by genetic engineering, and of α-interferons from culture supernatants of induced mammalian cells, which comprises partition of appropriate crude substances containing interferon between an aqueous urea solution, which contains a surfactant, and a mixture of n-butanol and glacial acetic acid which contains water, and isolation of the purified α-interferons from the upper phase.

10 Claims, No Drawings

PROCESS FOR THE ISOLATION AND PURIFICATION OF ALPHA-INTERFERONS

Interferon was discovered as long ago as 1956, by Isaacs and Lindemann, as an indirect inhibitor of intracellular virus multiplication. Since then, many different types of interferon of natural origin have been identified, and these are classified, in particular, by the different cells of origin, as follows:

α-interferons from leukocytes
β-interferons from fibroblasts and
γ-interferons from lymphocytes.

Chemically, the interferons, which are induced in the particular cells by appropriate stimuli, belong to the group of glycoproteins, and some of them are stable to acid (pH 2) and display their full antiviral action of $10^8$–$10^9$ IU/mg in a species-specific manner. The primary structures of some α-, β- and γ-interferons, which are constructed of 146–166 amino acids, have been elucidated. In addition, interferons which do not occur naturally have been disclosed, either the structure of these having been shortened or the amino acid sequence having been modified, compared with natural interferons, by genetic engineering means.

The most recent work in the area of genetic engineering, in which interferon genes have been induced to undergo expression in $E.\ coli$, has shown that the glycosyl or polysaccharide side chains detected in the natural interferons appear to have no effect on the biological activity of the proteins. Moreover, the measured binding to non-glycosylated interferons from $E.\ coli$ of antibodies which have been raised using the natural glycoprotein is comparable, which points to the predominant effect of the protein structure of the interferon as the antigenic determinant.

Because of their therapeutic power, the interferons are produced on a large scale in industry either by harvesting of culture media of appropriate cell cultures or, recently, by fermentation of $E.\ coli$ strains into which an interferon-coding ONA vector has been cloned by genetic engineering means. The processes generally used for the isolation and purification of the crude interferon preparations obtained (mean activity $10^3$–$10^4$ IU/mg protein) are affinity and adsorption chromatography. These make use of the special ability of interferon to bind with high specificity to immobilized hydrophoic ligands, metal ions, thiols, organic mercury compounds, polynucleotides and controlled pore glass and to antibodies. However, in spite of the variety of purification methods, the yields and purity of the interferons thus obtained remain unsatisfactory, as is shown by the uncertainty about the cause of the side effects in the clinical trials of interferons on humans.

For this reason, new and effective isolation processes are necessary. This objective is achieved by the present invention of a process for the enrichment and isolation of interferons, whch comprlses dissolving freeze-dried crude mixtures containing interferon in an aqueous solution of urea which contains a surfactant, such as sodium dodecyl sulfate (SDS), and obtaining the interferon from this solution by extractive two-phase partition using a mixture comprising n-butanol/glacial acetic acid/H$_2$O. This entails enrichment of the interferon in the butanol-containing phase, and it can be isolated from this after dilution with water and dialysis by subsequent freeze-drying. The process according to the invention is superior to the known affinity and adsorption processes in that it makes possible the elimination of more than 95% of all the concomitant contaminants from the $E.\ coli$ fermentation in an effective and one-stage enrichment step.

Thus the invention relates to a process for the isolation and purification of α-interferons generated by plasmids from bacterial cultures which have been modified by genetic engineering, and of α-interferons from culture supernatants from induced mammalian cells, which comprises partltion of appropriate crude substances containing interferons between an aqueous urea solution, which contains a surfactant, and a mixture of n-butanol and glacial acetic acid which contains water, and isolation of the purified α-interferons from the upper phase.

Using the process according to the invention, it is preferred to separate mixtures of α-interferons generated by plasmids (in this context, this is also to be understood to include hybrid α-interferons) from the contaminants which result on obtaining them from disrupted bacteria and fermentation broths.

A particularly suitable two-phase organic/aqueous solvent system is composed of an aqueous lower phase which contains 1 to 8 mol/l urea and an anionic surfactant, preferably an alkyl sulfate, in particular sodium dodecyl sulfate (SDS), for example in a concentration of 0.1–2% by weight, and an aqueous/organic upper phase which is preferably saturated with water and composed of n-butanol and glacial acetic acid, preferably 300 to 400 parts by volume of n-butanol and 30 to 50 parts by volume of glacial acetic acid, in particular about 350 parts by volume of n-butanol and 40 parts by volume of glacial acetic acid.

The interferon thus extracted in the upper phase can then be isolated by dilution with water and removal of salts by dialysis and freeze-drying.

If it is intended to purify the preparation further, it is possible to subject the upper phase which contains interferon to, for example, further partition, preferably between it and an organic/aqueous phase containing n-butanol and glacial acetic acid. Solvent systems of the following composition have proved to be particularly suitable:

n-Butanol: 200 to 230, preferably about 215, parts by volume

Glacial acetic acid: 165 to 185, preferably about 175, parts by volume

Water: 2,000 to 2,300, preferably about 2,150, parts by volume.

The further purification can be carried out by, for example, using a droplet countercurrent partition with the abovementioned aqueous system as the stationary phase.

Another option for final purification is chromatography on a partition column which is packed with, for example, Sephadex$^{(R)}$ LH 20, equilibrated with, for example, n-butanol/glacial acetic acid/H$_2$O (about 215:175:2,150, vol./vol.). For this purpose, the upper phase from the extraction, which contains interferon, is applied directly to the partition column, and the column is developed using fresh upper phase.

The process according to the invention is particularly advantageously applied to the removal of α-interferons from fermentations of $E.\ coli$ strains which have been modified by genetic engineering.

EXEMPLARY EMBODIMENTS

EXAMPLE 1

The lysate of a 10 l fermentation of an *E. coli* strain which produces α-interferon generated by a plasmid is centrifuged. The clear supernatant is then freeze-dried. Yield 13 g.

The interferon content of this material measured by the reduction in the cytopathic effect (Lin et al. J. Gen. Virol. 39, 125–130, 1978) is $2 \times 10^8$ IFU/g of substance.

10 g of the crude material are suspended in 50 ml of aqueous 6M urea solution (1% SDS) with vigorous stirring, and the insoluble fraction is removed by centrifugation. The solution is adjusted to about pH 3 by addition of glacial acetic acid. The resulting precipitate is stirred at 40° C. for 15 minutes, centrifuged and again taken up in 50 ml of 6M urea solution (1% SDS). An equal volume of the upper phase composed of n-butanol and glacial acetic acid (=350:40; saturated with water) is poured onto the clear solution. The two phases are thoroughly mixed at 40° C. for 30 minutes and then separated by renewed centrifugation. The upper phase is removed, diluted with water, dialyzed and freeze-dried. The residue (8 mg) is composed of α-interferon which is about 75% pure and has a CPE value of $2 \times 10^8$ IFU/mg of substance. This material can now be chromatographed in a customary manner, for example on an affinity column onto whose support material antiinterferon antibodies have been covalently immobilized. The purity after this is more than 95%. The interferon thus obtained shows a homogeneous band on SDS gel electrophoresis.

EXAMPLE 2

10 g of crude material are worked up as in Example 1 by partition between the upper phase and 6M urea solution (1% SDS). The upper phase containing interferon is fed into a DCC chromatograph (droplet countercurrent; for example Büchi 670). The stationary phase in the DCC chromatograph is composed of n-butanol glacial acetic acid/water (215:175:2,150 parts by volume). The partition is developed using fresh upper phase. The eluate containing interferon is collected using a fraction collector. The appropriate fractions are combined and the interferon is isolated by freeze-drying as in Example 1.

Yield: 12 mg of interferon with a content of 63%.

We claim:

1. A process for the isolation and purification of α-interferons generated by plasmids from bacterial cultures which have been modified by genetic engineering, and of α-interferons from culture supernatants from induced mammalian cells, which comprises partition of crude materials containing α-interferon between an aqueous urea solution, which contains an anionic surfactant, and a mixture of n-butanol and glacial acetic acid which contains water, and isolation of the purified α-interferons from the upper phase.

2. The process as claimed in claim 1, wherein α-interferons are isolated and purified from crude materials derived from bacterial cultures containing plasmids which have been modified by genetic engineering.

3. The process as claimed in claim 2, wherein hybrid α-interferons are isolated and purified.

4. The process as claimed in claim 1, wherein the lower phase contains 1 to 8 mol/l urea.

5. The process as claimed in claim 1, wherein the lower phase contains an anionic surfactant.

6. The process as claimed in claim 1, wherein the lower phase contains 0.1 to 2% sodium dodecyl sulfate.

7. The process as claimed in claim 1, wherein the upper phase is a mixture composed of n-butanol and glacial acetic acid, in the ratio by volume of about 350:40, which contains water.

8. The process as claimed in claim 1, wherein the mixture of n-butanol and glacial acetic acid is saturated with water.

9. The process as claimed in claim 1, wherein the upper phase containing α-interferon is subjected to a further partition between it and an organic/aqueous phase containing n-butanol and glacial acetic acid.

10. The process as claimed in claim 9, wherein this organic/aqueous phase is a mixture composed of n-butanol/glacial acetic acid/water in the ratios by volume of about 215:175:2,150.

* * * * *